United States Patent [19]

Kiovsky et al.

[11] Patent Number: 4,526,690
[45] Date of Patent: Jul. 2, 1985

[54] APPARATUS FOR NUCLEIC ACID QUANTIFICATION

[75] Inventors: Joseph R. Kiovsky, Nashua, N.H.; Clifford L. Hendrick, Boxborough, Mass.

[73] Assignee: Millipore Corporation, Bedford, Mass.

[21] Appl. No.: 463,747

[22] Filed: Feb. 4, 1983

[51] Int. Cl.³ .............................................. B01D 31/00
[52] U.S. Cl. .................. 210/335; 210/433.2; 210/489; 210/492; 210/927; 422/101
[58] Field of Search .................. 210/321.1, 335, 433.2, 210/488–492, 927; 422/101

[56] References Cited

U.S. PATENT DOCUMENTS

| Re. 30,562 | 3/1981 | Park | 435/296 |
|---|---|---|---|
| 3,649,464 | 3/1972 | Freeman | 195/40 |
| 4,154,795 | 5/1979 | Thorne | 422/102 X |
| 4,220,535 | 9/1980 | Leonard | 210/321 |
| 4,245,064 | 1/1981 | Drobnik et al. | 525/329 |
| 4,246,339 | 1/1981 | Cole et al. | 422/102 X |
| 4,276,048 | 6/1981 | Leaback | 435/291 |
| 4,302,204 | 11/1981 | Wahl et al. | 422/56 |
| 4,304,865 | 12/1981 | O'Brien et al. | 435/285 X |
| 4,338,094 | 7/1982 | Elahi | 422/57 |

OTHER PUBLICATIONS

Millipore Catalogue and Purchasing Guide, 1977, First Printing Dec. 1976, Cat. No. MC177/u, Millipore Corp., Bedford, MA 01730, p. 48.

Primary Examiner—David Sadowski
Attorney, Agent, or Firm—Andrew T. Karnakis; Paul J. Cook

[57] ABSTRACT

A multiwell apparatus for the assay of microliter quantities of body fluids is provided which prevents fluid loss by lateral migration or gravity flow through a microporous membrane or ultrafilter. A sample is passed through a membrane to which an antibody has been bonded in order to harvest complementary viral antigens in the sample. The harvested viral antigen is converted to single strand DNA or RNA which then is deposited on a second membrane. The deposited single strand DNA or RNA is capable of reacting with labeled DNA or other suitable detection probe which can be detected and correlated with antigen concentration in the sample.

10 Claims, 5 Drawing Figures

APPARATUS FOR NUCLEIC ACID QUANTIFICATION

BACKGROUND OF THE INVENTION

The invention relates to a method and apparatus useful in the assay of DNA or RNA and is particularly concerned with multiwell filtration devices capable of performing a plurality of assays simultaneously.

Test plates for in vitro analysis which contain a multiplicity of individual wells or reaction chambers are commonly known laboratory tools. Such devices have been employed for a broad variety of purposes and assays as are exemplified by U.S. Pat. Nos. 3,649,464; 4,304,865; 4,276,048; 4,154,795; and Re 30,562. Microporous membrane filters and filtration devices containing such microporous membranes have become especially useful with many of the recently developed cell and tissue culture techniques and assays - particularly those in the fields of virology and immunology.

Multi-well filtration plates have been used to conduct multiple assays simultaneously some of which last several hours before filtration is actually performed. With such filtration plates, especially those containing microporous membranes, there is a well recognized and recurrent problem in that fluids in the wells tend to pass through the membrane by gravity flow thereby causing a loss of contents from within the reaction well before the desired stage in the experimental design. Membranes at the bottom of wells in other devices lose liquid by gravity flow and also by lateral migration to adjacent wells thereby causing cross-contamination. Prevention of fluid loss through the membrane in this manner is vitally important when the assay utilizes very small sample volumes as reactants, since such test samples often are less than 100 microliters in volume. The pendant drop that invariably forms on the underside of the microporous membrane due to such capillary action and gravity flow is typically about 50 microliters in volume and it is apparent that a fluid loss of such proportions must drastically affect the assay.

Presently, there are available hybridization techniques for detecting single strand DNA or RNA molecules including single strand viral DNA or RNA molecules. Generally hybridization involves the steps of binding single strand DNA or RNA molecules to a substrate such as nitrocellulose and thereafter mixing the bound DNA or RNA with a liquid containing labeled complementary single strand DNA or RNA molecules. The degree of binding of the complementary single strand DNA molecules is measured by measuring the amount of marker on the substrate. By operating in this manner, it is possible to assay for either the single strand DNA or RNA bound to the substrate or the DNA or RNA in the liquid. Such a technique is described, for example, in U.S. Pat. No. 4,302,204. Prior to the present invention, there has been no efficient and reliable method to assay for the presence of virus in the blood. This is primarily due to interference of the hybridization reaction by a variety of blood serum proteins.

Accordingly, it would be desirable to provide an efficient and reliable method to assay for virus, particularly for virus in blood.

SUMMARY OF THE INVENTION

A filtration apparatus for the assay of microliter quantities of DNA or RNA is provided comprising a plate having a plurality of apertures open at each end, a first liquid permeable substrate having bound thereto antibody to the substance being assayed. The liquid permeable substrate is disposed across and sealed about one end of each aperture thereby forming a well with a discrete substrate area and a hydrophobic fabric disposed across and bonded adjacent to the substrate area bounded by each well. The hydrophobic fabric prevents a loss of fluid by lateral migration and/or gravity flow from within the well in the absence of an applied differential pressure. Additionally provided are a second liquid permeable substrate upon which single strand DNA or RNA can be bound and a guiding projection which directs such fluid as passes through the first substrate means to the second substrate means.

In use, the sample to be tested is filtered through the first substrate in order to bind the microbiological material containing DNA or RNA to its antibody bound to the substrate and the filtrate is discarded. The first substrate then can be washed to remove blood serum proteins or other components that interfere with hybridization reactions. The second substrate and the guiding projection then are positioned below each of the first substrates and the bound microbiological material is contacted with a reagent that converts DNA or RNA to single strand DNA or RNA so that it can be bound to the second substrate. A labeled DNA or RNA probe complementary to the bound single strand DNA or RNA then is contacted with the second substrate to bind with the available single strand DNA or RNA. The second substrate then is monitored for radioactivity or other detection method which then is correleted to DNA or RNA concentration (microbiological material concentration) in the original sample.

In a preferred form of this invention, the first substrate comprises a cellulose acetate membrane to which an antibody is bound through a divinylsulfone bridge and the second substrate comprises nitrocellulose to which single strand DNA or RNA can be bound.

DESCRIPTION OF THE FIGURES

The present invention may be best understood when taken in conjunction with the accompanying drawings, in which.

DETAILED DESCRIPTION OF THE EMBODIMENTS

The invention is an improvement in filtration apparatus having at least one reaction well which contains a first microporous membrane having an antibody bound thereto and adapted for the separation, selection and retention of a complementary antigen to the bound antibody from fluids. Attached adjacent to the first microporous membrane is a porous hydrophobic fabric which is positioned either above or preferably below the first microporous membrane. This hydrophobic fabric prevents fluid loss by lateral migration or gravity flow through the membrane in the absence of a vacuum force but will still allow diffusion of gases into or out the interior of each well on the plate.

Figure 1:
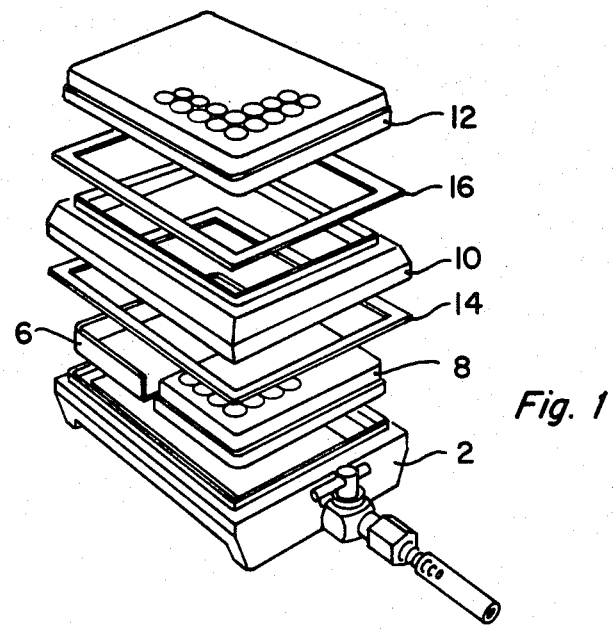
FIG. 1 is an exploded view of a vacuum assembly useful with this invention.

Embodiments of the invention are most useful with the vacuum assembly shown in FIG. 1 which is capable of simultaneously processing 96 individual test samples of up to 440 microliters (ul) each. The vacuum assembly comprises a base 2 which acts as a vacuum chamber and contains a hose barb for connection to a regulated external vacuum source. Housed within the base 2 are tray 6 and/or a receiving plate 8 having up to 96 individual chambers each containing a second microporous membrane upon which single strand DNA or RNA can be deposited. A filter support 10 holding a 96-well filtration plate 12 lies above the tray 6 separated by gaskets 14 and 16 which form an airtight seal in the presence of a vacuum force.

Figure 2:
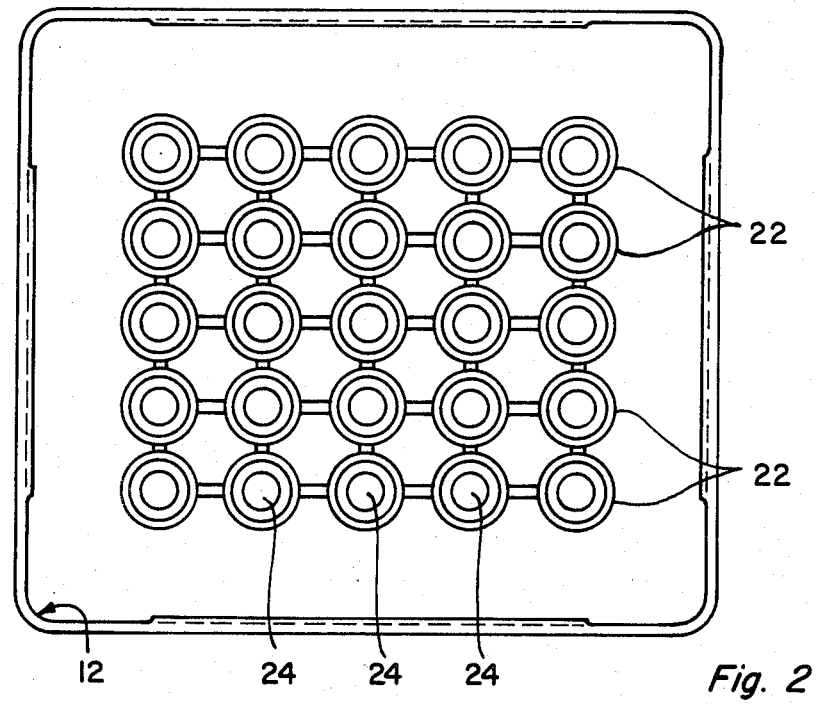
FIG. 2 is an overhead view of a filtration apparatus comprising one embodiment of the present invention.
Figure 3:
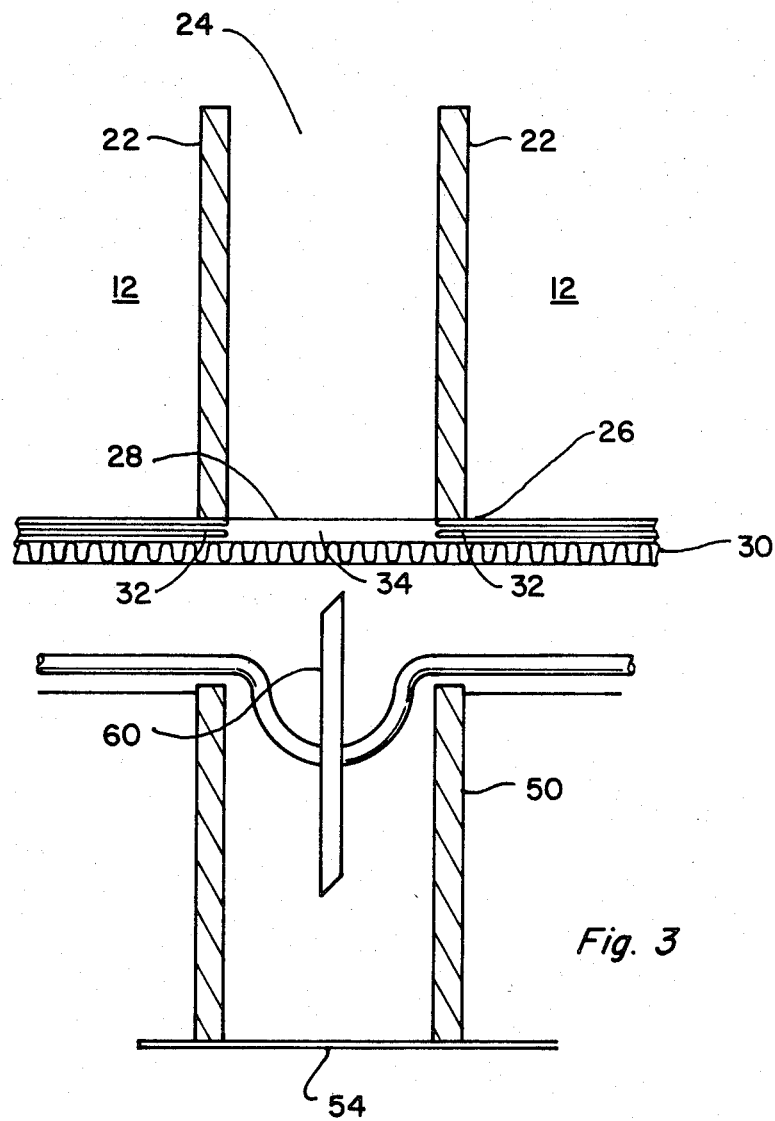
FIG. 3 is a cross-sectional view of the preferred filtration apparatus comprising the present invention.

Detailed views of the filtration plate utilizing the preferred embodiment of the present invention are shown in FIGS. 2 and 3. It will be appreciated that the number of wells found in the filtration plate 12 are simply a matter of convenience for the investigator. The plate 12 may contain as few as one well or as many wells as are functionally permissible given the actual dimensions of the plate. The filtration plate 12 may be formed of any resilient and nonreactive material commonly available, the composition of choice being a matter of convenience or economics only. Each well 22 comprises an aperture 24 through the entire depth of the plate 12, the thickness of the plate 12 determining the volume of fluid to be retained within the well. The diameter of the aperture will vary to meet the user's needs but typically will range from 3 to 25 millimeters in diameter. The first microporous membrane filter 26, is disposed across and sealed about the aperture 24 in the plate 12 such that the area across each well will serve as a filtering area 28. Methods of bonding the microporous membrane 26 to the plate 12 and sealing it about the perimeter of the aperture 24 are well known in the art and need not be described in detail here. The composition and flow characteristics of the first microporous membrane 26 forming the filtering area 28 across each aperture 24 is also a matter of choice. Cellulose acetate, polyamides and polyvinylidene fluoride microporous membranes or the like can be used for binding antibody thereto. The cellulose acetate is the preferred first microporous membrane since antibodies can be easily and efficiently bound thereto through a divinylsulfone bridge. The porosity of the membrane will be selected with a view to the chosen application. Although membranes having a pore size of 0.025 to 10.0 micrometers and a thickness of 50 to 200 micrometers are favored, the first microporous membrane 26 are not limited to microporous membranes as such. Rather, ultrafiltration media can be utilized in lieu of microporous membrane. By the term ultrafiltration media is meant a material capable of retaining a molecule in solution. Such ultrafiltration media are useful for retaining molecules as small as about 100 daltons and generally molecules as large as about two million daltons. Examples of such ultrafiltration media are well known in the art and include polysulfone and other polymeric materials available from Millipore Corporation under the registered trademark, PELLICON ®. All that is necesary is that the membrane 26 be capable of binding to antibody of the microbiological material being assayed and that it does not retain materials which interfere with the hybridization interaction with or without a washing step. It will be appreciated by those ordinarily skilled in the art that the individual membrane filter 26 bounded by each well 22 can be removed via a filter punch after filtration for further processing if necessary.

The apparatus shown in FIG. 3 is the configuration utilized after the antigen has been bound to the antibody on the first membrane 26 and after the first membrane 26 has been washed free of materials that interfere with the hybridization interaction and when it is desired to deposit single strand RNA or DNA on second membrane 54. As can be seen in FIG. 3, a hydrophobic fabric 30 is disposed across and bonded adjacent to the filtering areas 28 of the well 22. Preferably, the hydrophobic fabric is bonded to the first membrane 26 abutting the perimeter of aperatures 24 such that a minute space 34 is created and maintained between the fabric 30 and the filtering area 28. The fabric 30 may be heat bondable with a paraffin film or the like 32 or adhesive can be utilized for bonding to the filtration means 26. A polypropylene web can be utilized to bond membrane 26 to fabric 30 rather than film 32. When the polypropylene web is utilized, a hole need not be formed therein since it is permeable to aqueous liquid. In addition, the fabric 30 may be formed of woven or a nonwoven materials and be composed any of hydrophobic polyester, polyolefin, polytetrafluoroethylene or other polymer.

After the antigen has been deposited on membrane 26, it is washed with a reagent that selectively removes the antigen and converts the antigen DNA and RNA to single strand DNA and RNA such as 1.0M sodium hydroxide, 1.0M potassium hydroxide or the like. The reagent carries the single strand DNA or RNA to membrane 54 such as nitrocellulose, polyvinylidene fluoride or nylon or the like and preferably nitrocellulose, where it is bonded. The bonded single strand DNA or RNA then is capable of reacting with a labeled DNA or RNA probe such as DNA labeled with biotin or with a radioactive label such as radioactive phosphorus or sulfur or the like.

It is preferred that attachment of the first membrane 26 and the hydrophobic fabric 30 to the receiving chamber 50 be performed as separate steps to insure their proper positioning and the formation of the minute space 34. Nevertheless, it is possible to attach both the first membrane and the hydrophobic fabric simultaneously, particularly if a heat bondable hydrophobic material is used as the fabric layer.

Affixation of a porous hydrophobic fabric in this manner permits the use of small sample volumes, often less than 100 microliters (hereinafter ul), to be used as reactants. Without the fabric layer, a drop of fluid approximately 50 ul in volume will collect below the filtration means as a pendant drop and become lost. With the hydrophobic fabric in place, the pendant drop that forms below the filtering area 28 as a result of capillary action and gravity flow will be substantially retained within minute space 34 and the tendency for liquid to pass through the filtering area is substantially reduced or entirely eliminated. As a result, assays during which the well contents require a fluid media incubation phase or a bathing of the reactants in fluid can be performed without errors or inconvenience.

Figure 4:
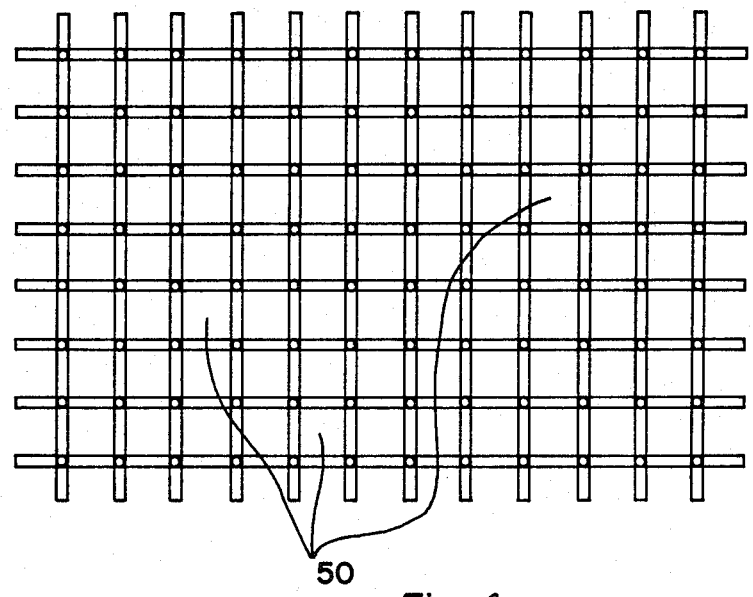
FIG. 4 is one embodiment of fluid collections means useful with the preferred embodiment illustrated in FIG. 3.
Figure 5:
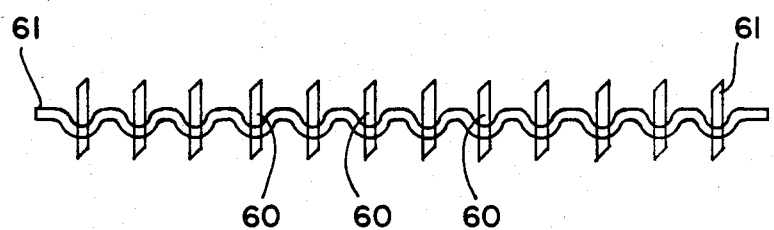
FIG. 5 is another preferred embodiment of the invention illustrated in FIG. 3.

Another aspect of the present invention is the pendant drop release fixture illustrated in FIGS. 3 and 5. This fixture is intended to be used with the multichambered fluid collection means shown in FIGS. 1 and 4 which is designed to receive filtrate from the interior of the well aligned directly above it via a plurality of individual receiving chambers 50. In this manner, the filtrate from each well will be separately analyzed. This compartmentalization feature alone, however, may not correct for the problem of comingling of filtrates deriving from different wells as the fluid is pulled through the hydrophobic fabric by an applied differential pressure. Similary, in those situations where the hydrophobic fabric is not present or is not necessary for the purposes of the assay, pendant drops will form and routinely collect on the underside of each filtering area. In small volume assays, the worker cannot afford to lose the 50 ul hanging as a drop from the membrane. Even in larger volume assays, an accidental movement or subsequent manipulations of the filter plate will dislodge the pendant drop and cause it to fall into the wrong receiving chamber causing cross-contamination of filtrates and erroneous test results.

Both these kinds of problems are corrected by placement of a pendant drop release fixture - in the form of a guiding projection 61 - between the filtering area 28 and the receiving chamber 50. The preferred embodiment of this guiding projection 61 appears in FIGS. 3 and 5 as a series of spikes 60 molded in a pattern corresponding to the individual filtering areas 28 in the plate 12. Each spike 60 serves a dual function: first, as a surface upon which the small volumes of fluid which would otherwise be lost as a pendant drop are collected and removed from the filtering area 28; second, as a guide by which the fluids forming a pendant drop are directed to the appropriate chamber 50. The projections 61 can be injection molded or a die cut assembly. Any molding polymer material such as nylon, polystyrene, polycarbonate and polyethylene may be used for making the guiding projections; however, a hydrophilic material is preferred because it promotes interception and guidance of the pendant drop.

It is expected that the hydrophobic fabric and the fluid guiding projection will be used in tandem in the majority of assays. Nevertheless, where retention of fluid within the well is not necessary, the pendant drop release fixture may be used alone to advantage.

The apparatus of this invention can be utilized by first introducing a sample containing the microbiological material to be assigned into well 22. If the sample does not contain material that interferes with DNA or RNA hybridization, the chamber 50 can be positioned as shown in FIG. 3. If such interfering material is present, chamber 50 is positioned so that it does not receive filtrate from well 22. The microbiological antigen bound to antibody on membrane 26 then is washed free of such interfering material. Thereafter, the microbiological antigen is contacted with a reagent that frees the microbiological antigen and converts the DNA or RNA of the microbiological antigen to single strand DNA or RNA. During this latter step, chamber 50 is positioned to receive the single strand DNA so that it is bound to membrane 54. Unbound material passes through membrane 54 to waste. The single strand DNA or RNA bound to the membrane 54 within each chamber 50 when is contacted with radiolabeled complementary single strand DNA or RNA thereby to effect hybridization with any bound single strand DNA or RNA bound to the second membrane 54. The deposited radioactivity then is measured and is correlated to concentration by means of a previously-established standard curve by any manner well known in the art.

In the preferred form of this invention an antibody is bound the a cellulose acetate first membrane through a divinylsulfone bridge. It has been found that when coupling antibody to the cellulose acetate under specified conditions, more efficient binding of antibody is effected without deactivating the antibody. This results in significantly increased recovery of antigen from a given sample. The cellulose acetate membrane is immersed in a 0.01 to 20% weight percent aqueous solution of divinylsulfone at a pH between about 8 to 13 for a period of time and at a temperature to effect significant divinylsulfone coupling, typically 30 minutes at room temperature. Excess divinylsulfone is rinsed from the membrane which then is saturated with antibody solution having a pH between about 8 and 12. The saturated membrane then is incubated under conditions to prevent evaporation, such as between non-permeable films for a time period and at a temperature to effect substantially complete antibody coupling to the cellulose acetate through the divinylsulfone bridge. Typical incubating conditions are two hours at room temperature or overnight at 4° C. The resultant product then can be stored by first soaking in buffered saline at about 7 pH and then stored at a temperature which does not deactivate antibody, e.g. 4° C.

What we claim is:

1. Apparatus comprising:
   a plate having a thickness and at least one aperture extending through the thickness of the plate;
   a first membrane selected from the group consisting of a microporous membrane and an ultrafiltration membrane and having an antibody coupled to said first membrane and disposed over one end of said at least one aperture in said plate such that at least one well having a discrete volume is formed;
   a hydrophobic fabric contiguous to said first membrane at said one end;
   a second plate defining at least one chamber, one of said at least one chamber being associated with one of said at least one aperture to receive all liquid passing through said at least one aperture, each said at least one chamber having a bottom comprising a second membrane selected from the group consisting of a microporous membrane and an ultrafiltration membrane and being capable of coupling to a single strand RNA or single strand DNA molecule.

2. Apparatus comprising:
   a plate having a thickness and at least one aperture extending through the thickness of the plate;
   a first membrane selected from the group consisting of a microporous membrane and an ultrafiltration membrane and having an antibody coupled to said first membrane and disposed across one end of said at least one aperture in said plate such that at least one well having a discrete volume is formed;
   a hydrophobic fabric contiguous to said first membrane at said one end;
   a second plate defining at least one chamber, one of said at least one chamber being associated with one of said at least one aperture, and positioned with respect to said at least one aperture to receive all liquid passing through said at least one aperture, each said at least one chamber having a bottom comprising a second membrane selected from the group consisting of a microporous membrane and an ultrafiltration membrane and being capable of coupling to a single strand RNA or single strand DNA molecule and;

a guiding projection aligned with each said at least one aperture and positioned beneath said first membrane to direct fluid passing through said first membrane to one of said at least one chamber.

3. The apparatus of any one of claims 1 or 2 wherein said first membrane is cellulose acetate and wherein said antibody is coupled to said first membrane with divinylsulfone.

4. The apparatus of any one of claims 1 or 2 wherein said second membrane is nitrocellulose.

5. The apparatus of any one of claims 1 or 2 wherein said antibody is an antibody to a virus.

6. The apparatus as recited in claim 1 or 2 wherein said first membrane is cellulose acetate and said second membrane is nitrocellulose.

7. The apparatus as recited in claim 1 or 2 wherein said hydrophobic fabric is selected from the group consisting of a polyester, a polyolefin and polytetrafluoroethylene.

8. The apparatus as recited in claim 1 or 2 wherein said hydrophobic fabric is heat bondable.

9. The apparatus as recited in claim 1 or 2 wherein said hydrophobic fabric is secured with adhesive.

10. The apparatus as recited in claim 1 or 2 wherein antibody is an antibody to a virus.

* * * * *